(12) United States Patent
Piacsek et al.

(10) Patent No.: US 7,574,249 B2
(45) Date of Patent: Aug. 11, 2009

(54) DEVICE-LESS GATING OF PHYSIOLOGICAL MOVEMENT FOR IMPROVED IMAGE DETECTION

(75) Inventors: Kelly Lynn Piacsek, Pewaukee, WI (US); Janice Chu, Waukesha, WI (US); Steven Gerald Kohlmyer, Waukesha, WI (US); Michael Joseph Cook, Oconomowoc, WI (US); Michael George Bonner, Wauwatosa, WI (US); Patrick Joseph O'Day, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 264 days.

(21) Appl. No.: 11/053,793

(22) Filed: Feb. 8, 2005

(65) Prior Publication Data

US 2006/0178575 A1 Aug. 10, 2006

(51) Int. Cl.
*A61B 5/05* (2006.01)
(52) U.S. Cl. .............. 600/425; 600/427; 600/428; 600/436; 382/128; 378/4; 250/363.03
(58) Field of Classification Search ............... 250/362, 250/363.4, 363.3, 586, 461.2; 600/425, 427, 600/428, 436; 382/128; 378/4, 8, 901
See application file for complete search history.

(56) References Cited

U.S. PATENT DOCUMENTS 6,026,142 A * 2/2000 Gueziec et al. ............... 378/8

6,661,866 B1 * 12/2003 Limkeman et al. ........... 378/19
6,798,199 B2 9/2004 Larson et al.
2005/0123183 A1 * 6/2005 Schleyer et al. ............. 382/131

OTHER PUBLICATIONS

Erdi et al. The CT Motion Quantitation of Lung Lesions and Its Impact on PET-Measured SUVs. J Nucl Med. 45: pp. 1287-1292. 2004.*
Klein et al. Fine-Scale Motion Detection Using Intrinsic List Mode PET Information . Mathematical Methods in Biomedical Image Analysis. p. 71-78. Dec. 9, 2001.*
Nehmeh, et al., "Effect of Respiratory Gating on Quantifying PET Images of Lung Cancer," The Journal of Nuclear Medicine, vol. 43, Jul. 2002, pp. 876-881.
Boucher, et al., "Respiratory Gating for 3-Dimensional PET of the Thorax . . . ," The Journal of Nuclear Medicine, vol. 45, Feb. 2002, pp. 214-219.
Nehmeh, et al., "Reduction of Respiratory Motion Artifacts in PET Imaging of Lung Cancer . . . " The Journal of Nuclear Medicine, vol. 44, Oct. 2003, pp. 1644-1648.
Nehmeh, et al., "Effect of Respiratory Gating on Reducing Lung Motion Artifacts in PET . . . ," Med. Phys. 29, Mar. 2002, pp. 366-371.
Reutter, et al., "Automated 3-D Segmentation of Respiratory-Gated PET Transmission Images," IEEE, Dec. 1997, pp. 2473-2476.

* cited by examiner

*Primary Examiner*—Brian Casler
*Assistant Examiner*—Parikha S Mehta
(74) *Attorney, Agent, or Firm*—Dean Small; The Small Patent Law Group

(57) ABSTRACT

A method of imaging an object using a medical imaging system is provided. The imaging method acquires a stream of sinogram data. Changes in the stream of sinogram data corresponding to movement of the object are detected. The method selects portions of the stream of sinogram data. An image of the object based on the selected portions of the sinogram data is generated.

36 Claims, 8 Drawing Sheets

US 7,574,249 B2

DEVICE-LESS GATING OF PHYSIOLOGICAL MOVEMENT FOR IMPROVED IMAGE DETECTION

BACKGROUND OF THE INVENTION

The present invention relates to diagnostic imaging methods and systems. In particular, the present invention relates to methods and systems for device-less gating of a stream of sinogram data.

At least some known Positron Emission Tomography (PET) and Computed Tomography (CT) systems experience image quality that is highly affected by physiological patient motion. Such image quality may affect the diagnosis. Lung nodules, cardiac wall features or other small features of interest that move due to physiological motion such as cardiac and respiratory motion, may appear unfocused or faint without proper corrections. By employing a cardiac and/or respiratory gating protocol during scan acquisition, images may be classified according to physiologic position in the cardiac/respiratory cycle. The gating technique may correct for motion artifacts in images. Also, the image pathway of the nodule or other features of interest may be tracked.

Respiratory gating can be accomplished through the use of many different devices, which detect chest wall motion, such as spirometers, bellows, ultrasonic devices, and external infrared camera systems. Setup and calibration of the devices and systems for monitoring physiological movement can be long and complicated, and is not typically used for all exams. Furthermore, when gating on different systems and/or at different times, errors may be introduced when attempting to plan therapy dynamically. However, without the detection of and correction for physiological motion, incorrect diagnoses may result.

BRIEF DESCRIPTION OF THE INVENTION

In one embodiment, a method of imaging an object using a medical imaging system is provided. The imaging method acquires a stream of sinogram data. Changes in the stream of sinogram data corresponding to movement of the object are detected. The method selects portions of the stream of sinogram data. An image of the object based on the selected portions of the sinogram data is generated.

In another embodiment, a medical imaging system is provided. A scanner acquires a stream of sinogram data. A processor detects changes in the stream of sinogram data corresponding to movement of the object and selects portions of the stream of sinogram data. A display processor generates an image of the object based on the selected portions of the stream of sinogram data.

A method for positron emission tomography/computed tomography (PET/CT) is provided. The PET/CT method scans an image to acquire a stream of sinogram data. Changes in the stream of sinogram data corresponding to movement of the object are detected. The method selects portions of the stream of sinogram data. An image of the object based on the selected portions of the sinogram data is generated.

DETAILED DESCRIPTION OF THE INVENTION

Figure 1:
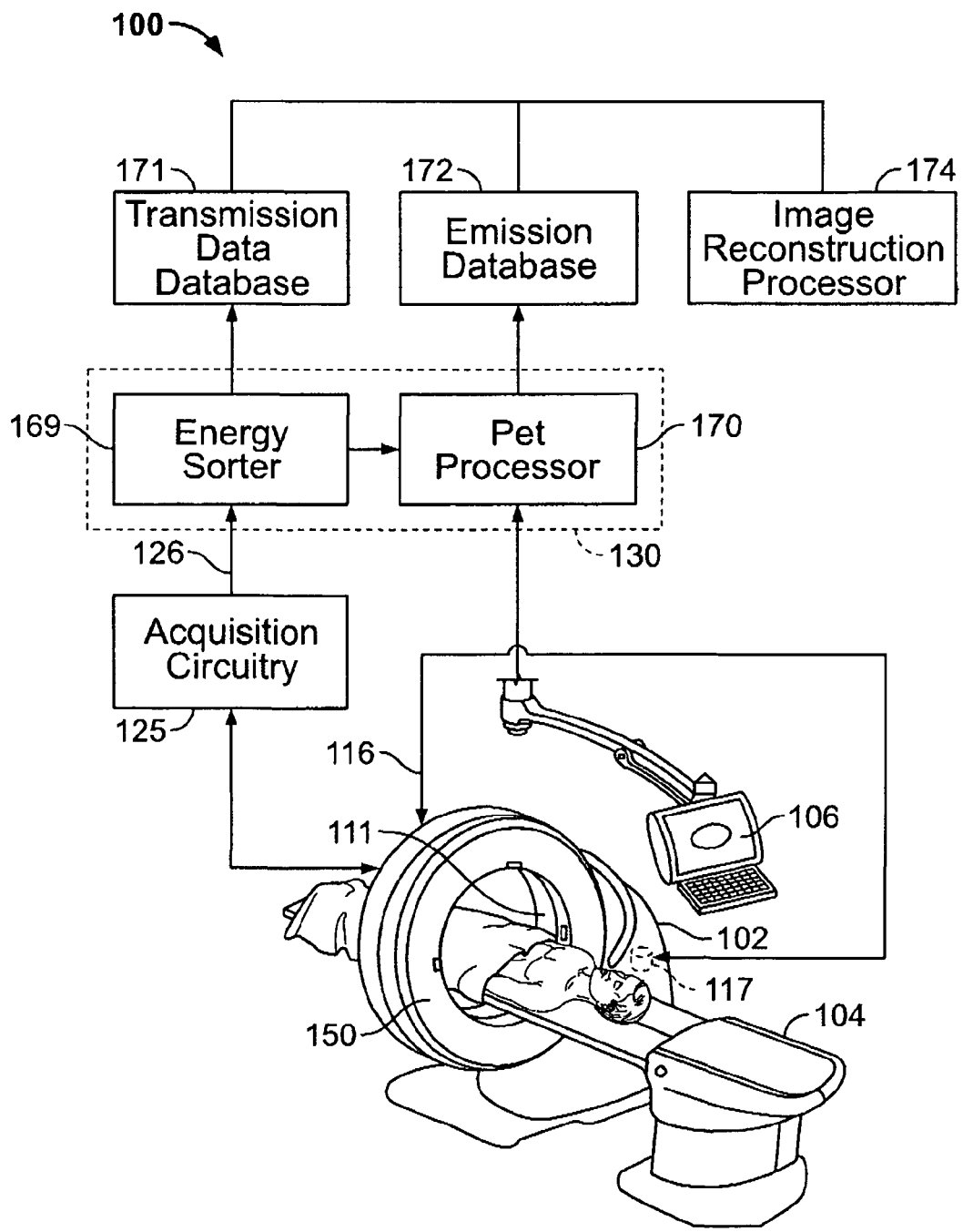
FIG. 1 is a schematic diagram illustrating a dual PET/CT global imaging system formed in accordance with an embodiment of the present invention. The system formed in accordance with an embodiment of the present invention may be any emission-type computed tomography imaging system including, but not limited to a single PET scanner, a single SPECT scanner or a dual SPECT/CT scanner.

FIG. 1 is a block diagram of a medical imaging system 100 formed in accordance with an exemplary embodiment of the present invention. The system formed in accordance with an embodiment of the present invention may be any emission-type computed tomography imaging system including, but not limited to a single PET scanner, a dual PET/CT scanner, a single nuclear (photon emission) computed tomography (SPECT) scanner or a dual SPECT/CT scanner. A medical imaging system 100 such as, for example, a positron emission tomography (PET) system, includes a gantry 102, a patient table 104 and a computer system 106. Gantry 102 provides mechanical support for mounting devices such as, for example, detectors, scanners and transmitters that are useful for scanning a patient. Gantry 102 houses imaging devices such as, for example, PET detectors. The PET system is a stationary annular detector with potential variant of a pin source for PET.

In accordance with an embodiment of the invention, a set of detectors such as, for example, PET detectors may be located on opposite sides of gantry 102. The PET detectors are then able to acquire image data by scanning the patient. The patient to be scanned lies on a patient table 104.

The imaging devices on gantry 102 acquire image data by scanning a patient lying on patient table 104. Moving patient table 104 enables the scanning of various parts of the patient. Directions of the motion of patient table 104 are as shown in FIG. 1. Patient table 104 lies along the axis of gantry 102, which is known as a viewing area axis (as shown in FIG. 1) and can be moved along this viewing area axis. Patient table 104 can be positioned at various axial positions along the viewing area axis. In an embodiment of the invention, gantry 102 includes a plurality of detectors that are fixedly spaced on gantry 102 positioned radially outward from the viewing area axis. In accordance with an embodiment of the invention, gantry 102 includes a plurality of detectors that are rotatable about the viewing area axis. This enables the scanning of various parts of the patient at different axial positions. CT, for example, is a rotating detector and source with a potential variant of a stationary detector ring for CT.

In an embodiment of the invention, computer system 106 handles the control, for example, the positioning of patient table 104. Specifically, computer system 106 is programmed to position patient table 104 at a plurality of axial positions along the viewing area axis. This positioning enables the scanning of different axial positions of the patient. Computer system 106 may further be programmed to keep a track of the position of patient table 104. Computer system 106 is also programmed to receive image data collected during scanning. The signal-to-noise ratio (SNR) of the collected data is also determined by computer system 106. Based on the SNR, computer system 106 is programmed to control the scanning. For example, computer system 106 may control the termination of a scan based on the SNR. In accordance with various embodiments of the invention, computer system 106 includes a Linux PC for user interface and custom array processor boards for image reconstruction.

A scan time may also be fixed or predetermined, for example, by a user or computer system 106. In case the user fixes the scan time, computer system 106 may receive an indication of the scan time. This may help computer system 106 to control the scanning. In addition to providing the scan time, the user may also provide computer system 106 an indication of the location of a volume of interest. The volume of interest is that part of the patient which is to be scanned. The volume of interest may be selected by a user and input to computer system 106.

In addition, medical imaging system 100 may include a transmission source. The transmission source is located such that the signals transmitted by the transmission source pass through the volume of interest of the patient. The signals may get attenuated when they pass through the patient. Hence, the detectors may collect data that is attenuated as data is collected after the transmitted signals pass through the patient. The transmission source is, thus, used to acquire attenuation data relative to the patient. In accordance with an embodiment of the invention, computer system 106 may be programmed to generate the attenuation data relative to a patient using the transmission source. Computer system 106 may further be programmed to determine the scan time for a frame of image data based on the attenuation data. Each frame of image data is a part of image data that corresponds to an axial position of patient. Moving patient table 104 along the viewing area axis enables the scanning of different axial positions of the patient. The positioning of patient table 104 is controlled by computer system 106.

The attenuation data is received by computer system 106. Computer system 106 may use the received attenuation data, for example, to determine the scan time for each frame of image data. Further, scan time of short scans may be determined based on the scan time determined for each frame of image data.

Various processors, sorters and databases are used to acquire and manipulate emission and transmission data. The processors, sorters and databases of FIG. 1 include acquisition circuitry 125, an acquisition processor 130, a transmission data database 171, an emission database 172 and an image reconstruction processor 174. Other computing components may be included with the system, which have been omitted here in the interest of simplification.

In one embodiment, when the energy corresponding to an intensity signal is above the X-ray range, sorter 169 provides the time, location and energy data to PET processor 170. Processor 170 generally uses the received data to identify pairs of data, also known as coincidence pairs, coincident pair lines and lines of response, corresponding to annihilation events that occurred inside the region of interest. After processor 130 identifies an annihilation event, processor 130 updates data in emission database 172 to reflect the annihilation.

After an acquisition session has been completed and complete sets of transmission and emission data have been stored in databases 171 and 172, respectively, image reconstruction processor 174 accesses the data in databases 171 and 172 and uses the accessed data to generate images that are requested by a system operator. The operator can use computer system 106 to select image types and views.

Figure 2:
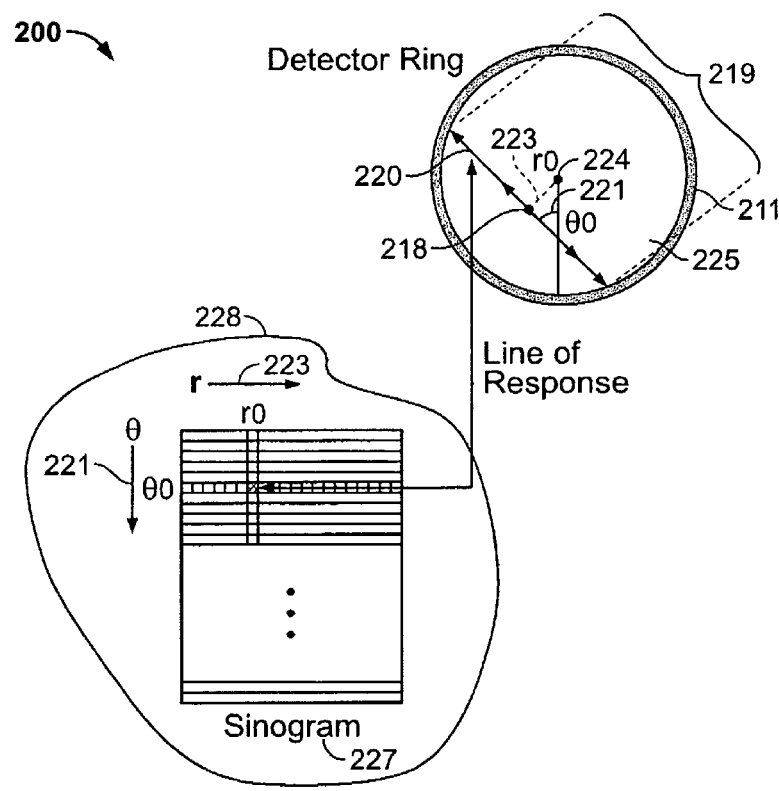
FIG. 2 is a perspective view of a detector ring and an illustration of the construction of a sinogram formed in accordance with an embodiment of the present invention.

FIG. 2 is a perspective view 200 of a detector ring 211 and an illustration 228 of the construction of a sinogram 227 formed in accordance with an embodiment of the present invention. In positron emission tomography (PET), sorter 169 of FIG. 1 receives a coincidence event pair 219 of an annihilation event 218 and identifies a corresponding line of response 220. Each line of response 220 may be identified by an angle θ 221 and a distance r 223 from a center 224 of the field of view 225. The array of the responses 220 is known as a sinogram 227.

System 100 has multiple rings 211 of detectors covering 15-25 centimeters in the axial direction. PET data may be acquired in either 2-dimensional or 3-dimensional mode. In 2-dimensional acquisition mode, lines of responses 220 occurring in the same ring 211 or immediately adjacent ring 211 are accepted; whereas in 3-dimensional mode, any line of response 220 occurring between any pair of detector rings 211 are acquired. In 2-dimensional, the coincident events 219 that are acquired within the same detector ring 211 contribute to the direct planes, while those events 219 across neighboring rings 211 contribute to the cross planes.

Figure 3:
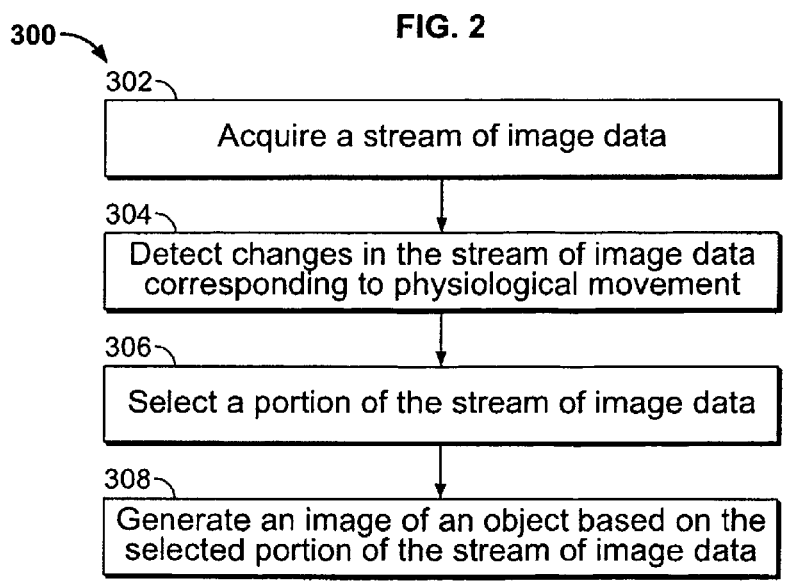
FIG. 3 is a flowchart of an exemplary method for respiratory device-less gating of a stream of sinogram data in accordance with an embodiment of the present invention.

FIG. 3 is a flowchart of an exemplary method 300 for respiratory device-less gating of a stream of sinogram data in accordance with an embodiment of the present invention. The technical effect of device-less gating is the detection of changes in an acquired stream of sinogram data corresponding to physiological movement, selection of a portion of the stream of sinogram data that minimizes physiological movement, and generation of an image of an object based on the selected portion of the stream of sinogram data. The technical effect of detection of changes in the stream of sinogram data corresponding to physiological movement eliminates laborious, time consuming and error prone manipulation of an external monitoring device to detect physiological movement. The technical effect is achieved by performing the set of sequential steps of method 300.

Using exemplary method 300, a stream of sinogram data is acquired 302. In one embodiment, the PET/CT system 100 acquires 302 a stream of sinogram data using positron emission tomography. Acquiring 302 lines of response 220 may include generating separate sinograms 227 for direct planes and cross planes in 2-dimension (2D), and separate sinograms 227 for all possible planes in 3-dimension (3D).

In an alternative embodiment, the PET/CT system 100 acquisition data may be stored in the form of list mode. List mode represents a capture by the PET detector 111 of coincidence event pairs 219 in the form of an ordered event list, for example, a chronologically ordered event list. List file events may be played back into a new scan prescription to produce derivations of the original scan. For example, the scan prescription may specify a different frame or bin size. Therefore, small sub-second sets of data may be evaluated, gaining higher temporal resolution. In one embodiment, an emission imaging system, e.g., PET/CT system 100, may acquire 302 a stream of sinogram data using an emission scan of the object. In another embodiment, a transmission imaging system, e.g., PET/CT system 100, may acquire 302 a stream of sinogram data using a transmission CT scan.

Method 300 detects, at 304, changes in the stream of sinogram data corresponding to physiological movement of the object. The detecting of changes in the stream of sinogram data may include measuring changes in simultaneous second modality reconstructed images including CT, x-ray and ultrasound. In one embodiment, method 300 may bin the stream of sinogram data into sinograms 227 and detect 304 changes in the sinogram data between sinograms 227 of at least one of computing a minimum width, calculating an area, determining a center area, determining a z-centroid, determining a y-centroid, computing a linear regression r squared of the edges, and calculating a sum of the square of the difference of the edges. In an alternative embodiment, method 300 may detect 304 changes in the sinogram data before or without binning the stream of sinogram data.

Method 300 selects, at 306, a portion of the stream of sinogram data. In one embodiment using PET, the coincidence event pairs 219 that occur in the prescribed scan may be divided into time intervals to create a predetermined number of sinograms 227. Each of the sinograms 227 is then examined and classified into a specific respiratory phase of a respiratory cycle. The respiratory cycle may be divided into time intervals or phases based on the detected 304 changes; and portions of the stream of sinogram data associated with the time intervals may be gated into associated bins or phases of the respiratory cycle. The time intervals or phases may be determined from a predetermined number of sinograms 227. For example, sinogram 227 may be classified into a specific respiratory phase by computing the minimum width or the area of the sinogram 227. Sinogram 227 analysis and classification into a specific respiratory phase may also be performed by calculating center area, z-centroid shift, shift in center of mass in z-direction, y-centroid shift, shift in center of mass in y-direction, linear regression r squared of the edges and sum of square of difference of the edges.

Method 300 generates, at 308, an image of the object based on selected 306 portions of the stream of sinogram data. In one embodiment, binning sinograms 227 into their respective respiratory phases may be accomplished by any standard means of binning dynamic data. For example, sinograms 227 may be binned using the amplitude or phase of the respiratory signal. In an alternative embodiment, a fixed forward method of binning may be used involving a trigger at the start of the signal and sequential binning of data according to time from trigger. In an alternative embodiment a pre-determined proportion (percentage) method of binning of the stored stream of sinogram data into respective phases of the respiratory cycle may be used involving a trigger or delay from a previous event at the start of the signal and sequential binning of data until a specific proportion of data from trigger has been generated. The binning method may define certain rejection parameters for eliminating unwanted outliers. For example, the method may reject acquisition data with amplitude greater than a specified amount, or reject triggers that indicate start of inspiration less than a certain specified time from the previous trigger. In an alternative embodiment, the method may define additional classification of the physiological signal determined from the sinogram data. Wherein, the respiratory signal estimated from the sinogram data or reconstructed image data may be used to diagnose physiologic characteristics of the patient. In another embodiment, an image may be generated 308 using at least one of the detected 304 changes in the stream of sinogram data to bin the sinogram data corresponding to a time interval or phase associated with physiological movement of the object.

Method 300 also generates, at 308 a waveform representing the respiratory or other physiologic motion of the organ being imaged. In one embodiment, said waveform is used to diagnose respiratory or other physiologic status of the patient being imaged.

In an alternative embodiment, another method of analyzing changes in the stream of sinogram data to generate a respiratory signal is to detect changes in the image reconstructed from the binned image data The image may be binned into a sinogram to reconstruct the image, for example, a PET image, and changes in the reconstructed image, for example, a PET image, may be detected. Changes in the stream of sinogram data may be detected by detecting changes in the stored or real-time reconstructed images, for example, CT images, at discrete time intervals corresponding to the stream of sinogram data. The image itself may be analyzed using the chest wall, or other structures to determine the respiratory motion. Simultaneously acquired image data or reconstructed images from other imaging modalities, for example, SPECT, X-ray CT, MR, planar X-ray, and ultrasound, may also be used to determine the respiratory motion.

In another embodiment, the acquired sinogram data or reconstructed image data may be filtered in multiple dimensions including space, volume and time prior to detection of changes to enhance the data contained in the datasets in order to improve detection of the respiratory signal.

Figure 4:
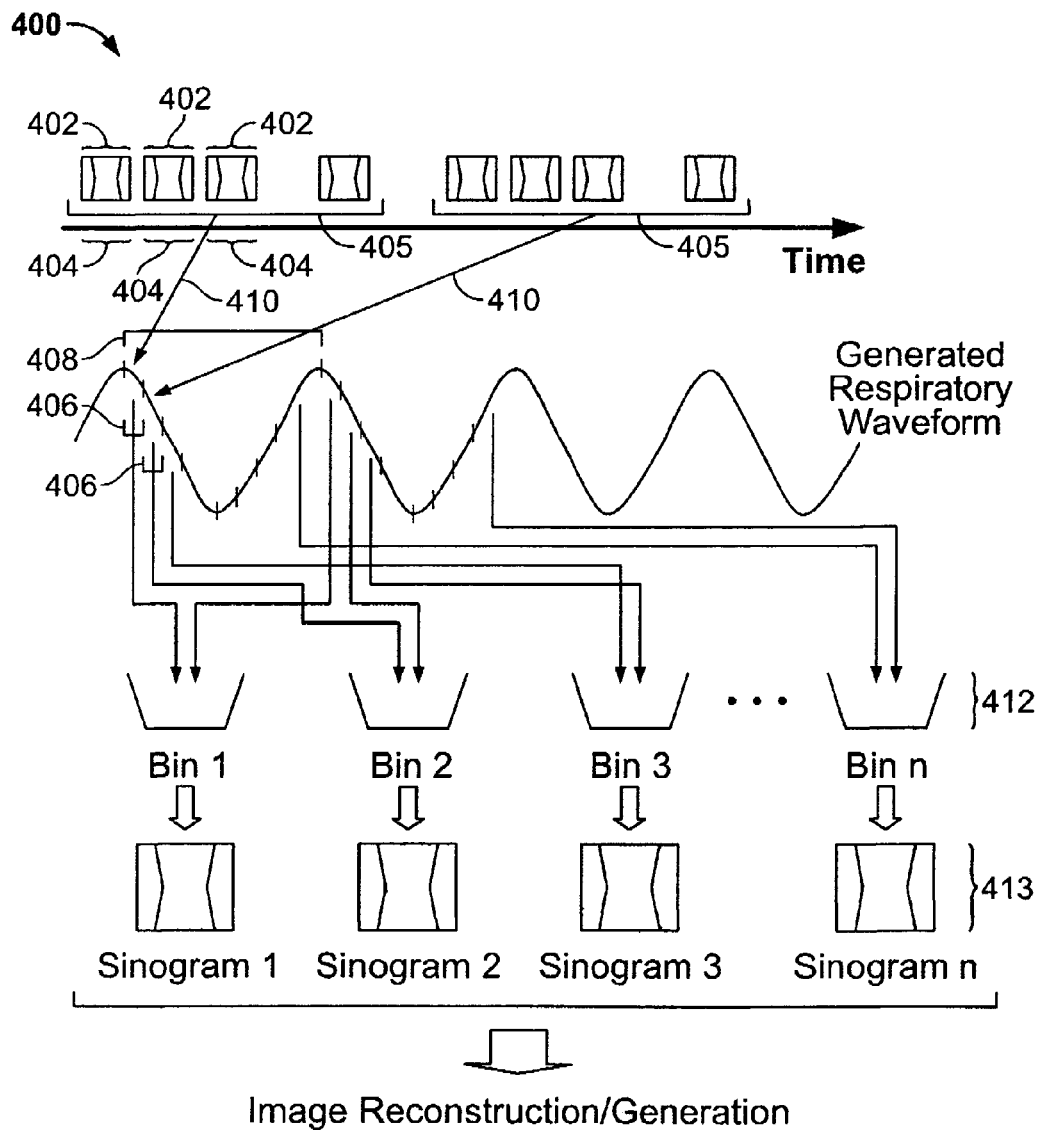
FIG. 4 is a respiratory gating map formed in accordance with an embodiment of the present invention.

FIG. 4 is a respiratory gating map 400 formed in accordance with an embodiment of the present invention. The coincidence event pairs 219 that are acquired 302 from a prescribed scan are divided into time intervals 404 to create a predetermined number of sinograms 402. Each sinogram 402 is then examined, e.g. changes detected 304, and classified or binned 410 into a specific respiratory phase/time interval 406. A respiratory cycle 408 is divided into respiratory time intervals 406 based on said detected 304 changes, and selected 306 portions 405 of the sinogram data associated with the respiratory time intervals 406 are gated or binned 410 into associated bins 412. The gated/binned data of bins 412 may be used to produce sinograms 413 and generate 308 images of the object.

Figure 5:
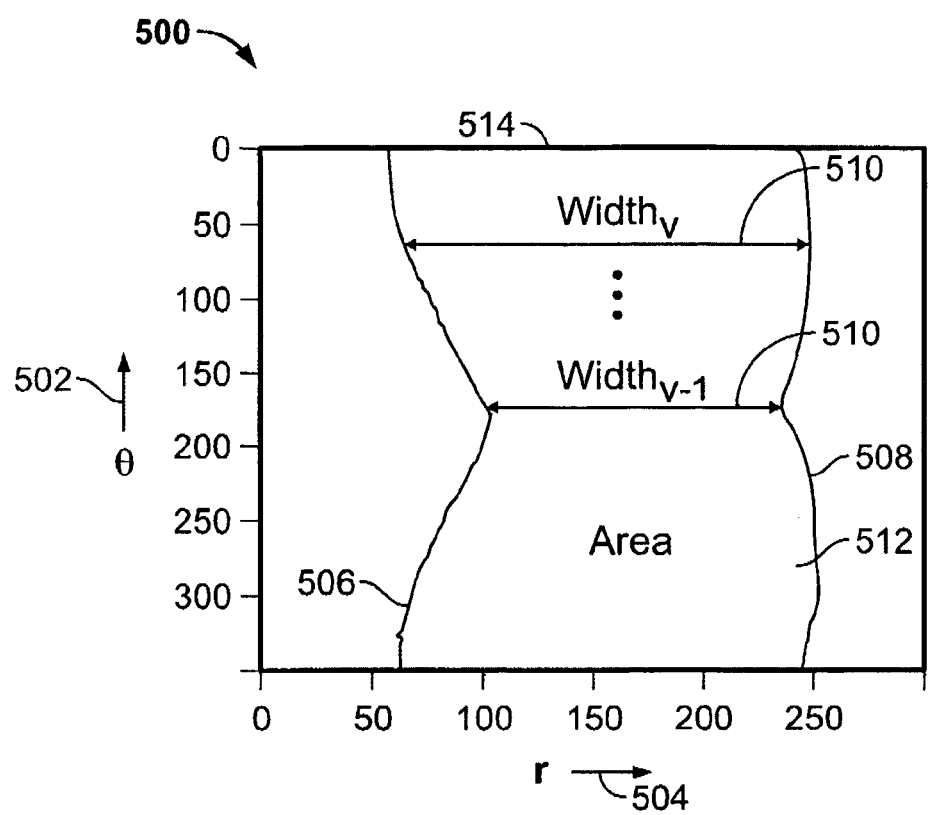
FIG. 5 is a sinogram plot illustrating a width and an area of a sinogram.

FIG. 5 is a sinogram plot 500 of a width 510 and an area 512 of a sinogram 514. Sinogram 514 is an enlargement of one of the sinograms 402 shown in FIG. 4. Examining and classifying sinogram 514 may be accomplished by calculating a width 510 and/or a minimum width 510 of sinogram 514. Width 510 of sinogram 514 is defined as the distance along an r-axis 504 of sinogram 514. Width 510 may be calculated for all θ 502. For example, computation of width 510 may employ an edge detection algorithm to detect edges 506 and 508 along the r-axis of sinogram. Width 510 may be obtained as the distance between edges 506 and 508 along the r-axis. The classification technique may also be accomplished by calculating area 512 of sinogram 514 instead of or in addition to the width 510. Area 512, defined as the sum of all widths 510, e.g. Area 512=summation over θ of widths 510. Area 512 may also be defined as a sum of a subset of widths 510 pertaining to a specific anatomic area of interest.

In another embodiment, classification may be accomplished by initial accumulation of a duration over multiple respiratory cycles; computing an average sinogram envelope; binning the stream of sinogram data into a sinogram at a particular slice or slab location along the length of the patient at a discrete time interval; computing a local sinogram envelope; and calculating the deviation above or below the average sinogram envelope. The local sinogram may be compared to the average sinogram such that excursions inside or outside of the average sinogram envelope may be classified in terms of expiration and inspiration, respectively, and the sinogram data corresponding to these events may be binned accordingly.

In yet another embodiment, classification may be accomplished by considering an average reconstructed CT image slice or slab along the length of the patient, wherein excursions inside or outside of the average CT-image envelope may be classified in terms of expiration and inspiration, respectively, and then sinogram data corresponding to these events may be binned accordingly.

Figure 6:
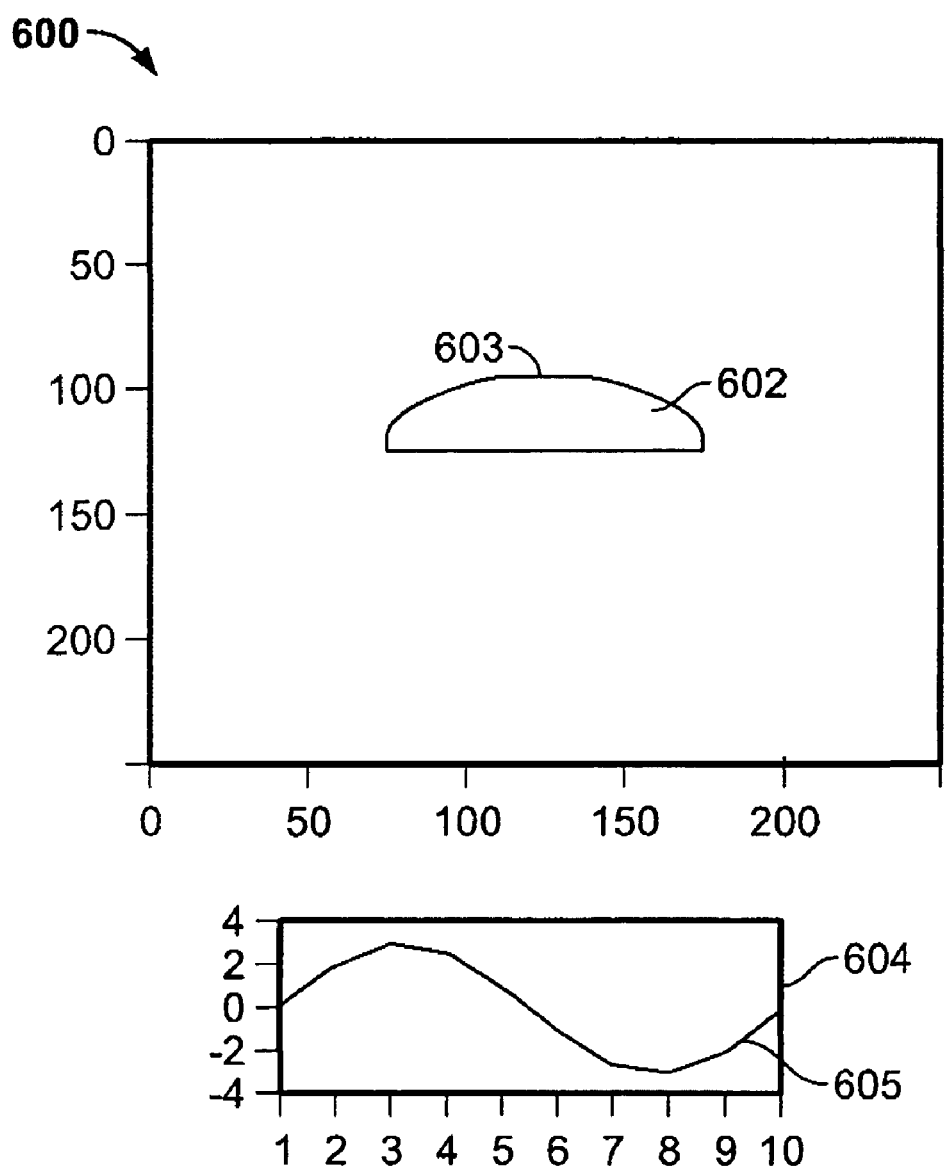
FIG. 6 is a view of a simulated phantom image.

FIG. 6 is a view 600 of a simulated phantom image 602. Phantom image 602 has a top curve 603 moving up and down in to simulate patient respiratory motion and is modeled by a sinusoidal motion 605 as shown in the small graph 604. Gated phantom images 602 of a physiological structure after image reconstruction over successive time intervals may be displayed to produce a simulation of physiological movement. In an alternative embodiment, gated phantom images 602 of a physiological structure after image reconstruction over successive time intervals may be displayed to produce a representation of physiological motion for diagnosis of respiratory events.

Figure 7:
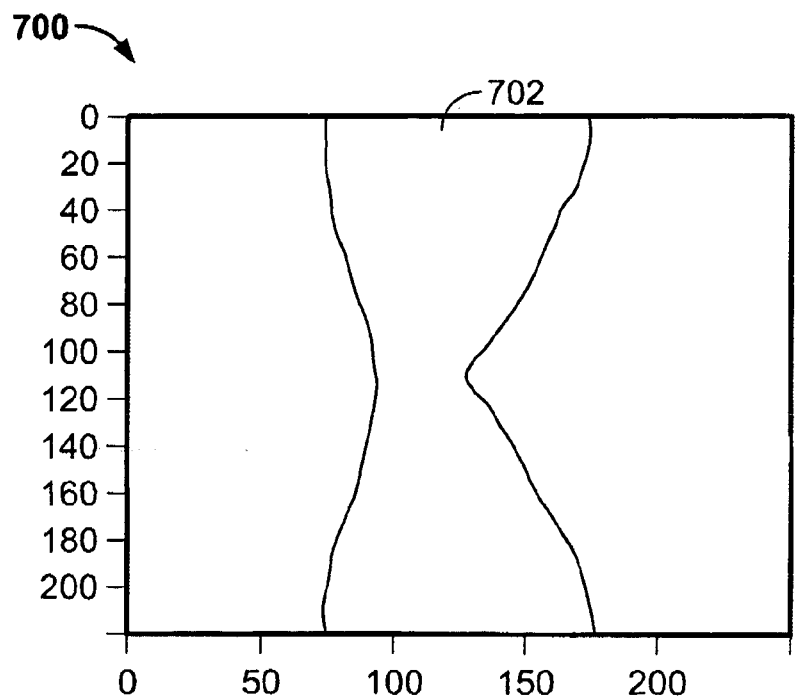
FIG. 7 is a view of a simulated sinogram.

FIG. 7 is a view 700 of a simulated sinogram 702. Using a parallel beam forward projection technique, multiple sinograms 702 are generated. The sinograms 702 change with patient motion. Gated sinograms 702 over successive time intervals are displayed to produce a simulation of physiological movement. In an alternative embodiment, gated sinograms 702 over successive time intervals are displayed to produce a representation of physiological motion for diagnosis of respiratory events.

Figure 8:
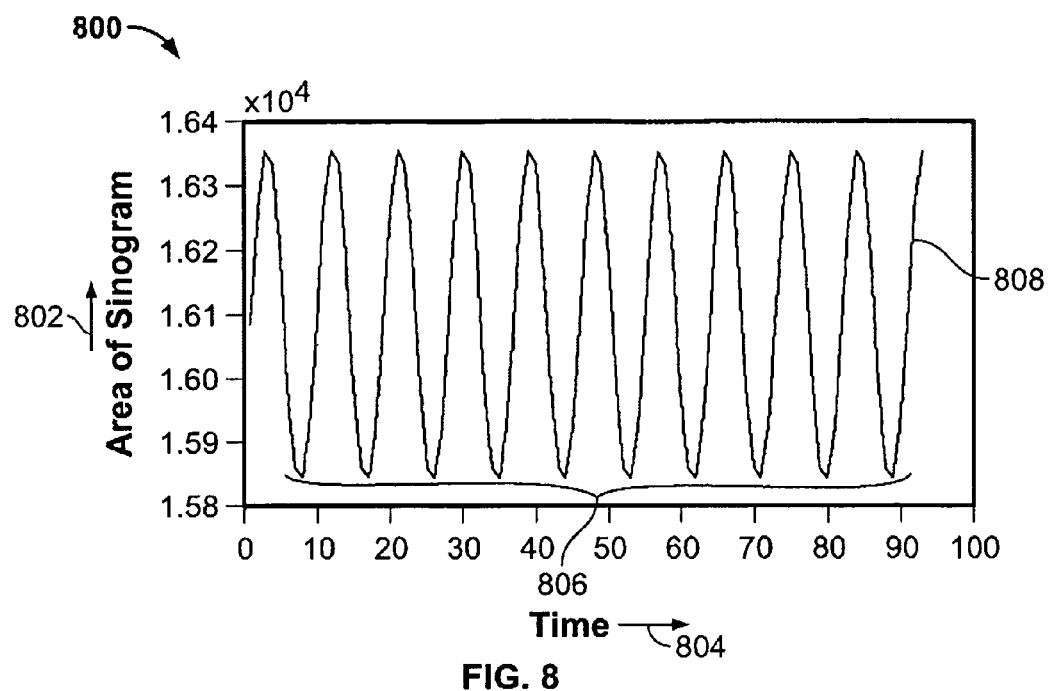
FIG. 8 is a graph representing sinogram area versus time (respiratory phase) formed in accordance with an embodiment of the present invention.

FIG. 8 is a graph 800 representing sinogram area 802 versus time 804 (respiratory phase) formed in accordance with an embodiment of the present invention. Graph 800 illustrates the area 802 of multiple sinograms over time 804 to produce ten respiratory cycles 806. Using the phantom sinograms, ten respiratory cycles 806 are created. Area 802 is calculated for each sinogram and a resulting generated respiratory waveform 808 shows a regular pattern.

Figure 9:
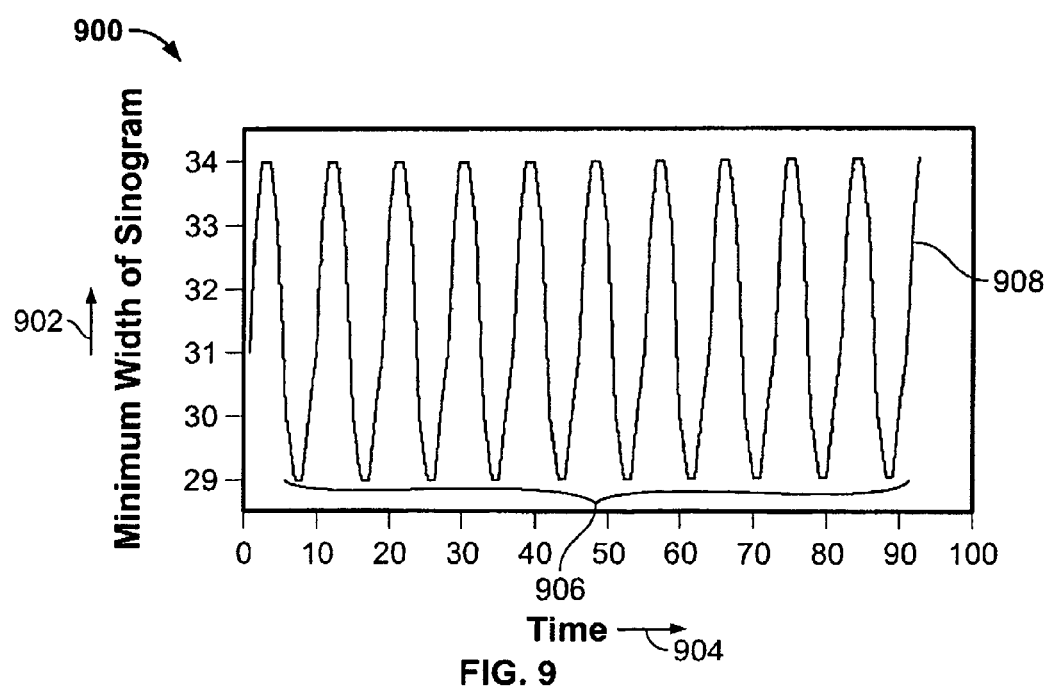
FIG. 9 is a graph representing sinogram minimum width versus time (respiratory phase) formed in accordance with an embodiment of the present invention.

FIG. 9 is a graph 900 representing sinogram minimum width 902 versus time 904 (respiratory phase) formed in accordance with an embodiment of the present invention. Graph 900 illustrates a minimum width 902 of multiple sinograms over time 904 to produce ten respiratory cycles 906. Using the phantom sinograms, ten respiratory cycles 906 are created. Minimum width 902 is calculated for multiple phases for each sinogram and a resulting generated respiratory waveform 908 shows a regular pattern.

Figure 10:
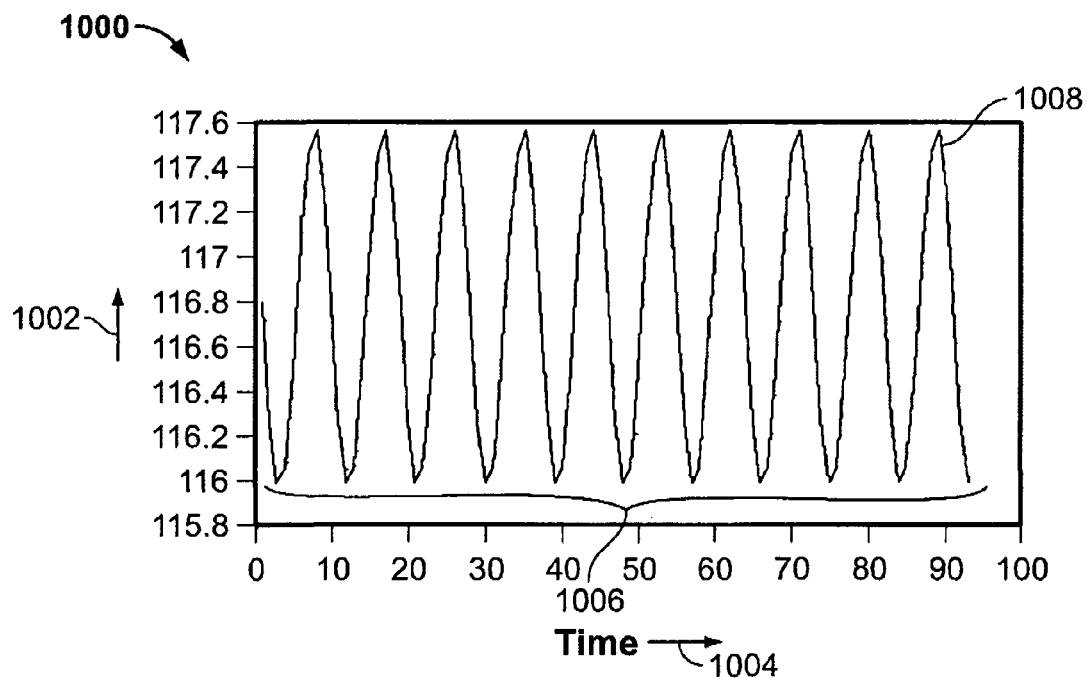
FIG. 10 is a graph representing sinogram y-centroid versus time formed in accordance with an embodiment of the present invention.

FIG. 10 is a graph 1000 representing sinogram y-centroid 1002 versus time 1004 formed in accordance with an embodiment of the present invention. Graph 1000 illustrates a y-centroid 1002 of multiple sinograms over time 1004 to produce ten respiratory cycles 1006. Using the ten phantom sinograms, ten respiratory cycles 1006 are created. Y-centroid 1002 is calculated for each sinogram and a resulting generated respiratory waveform 1008 shows a regular pattern.

Figure 11:
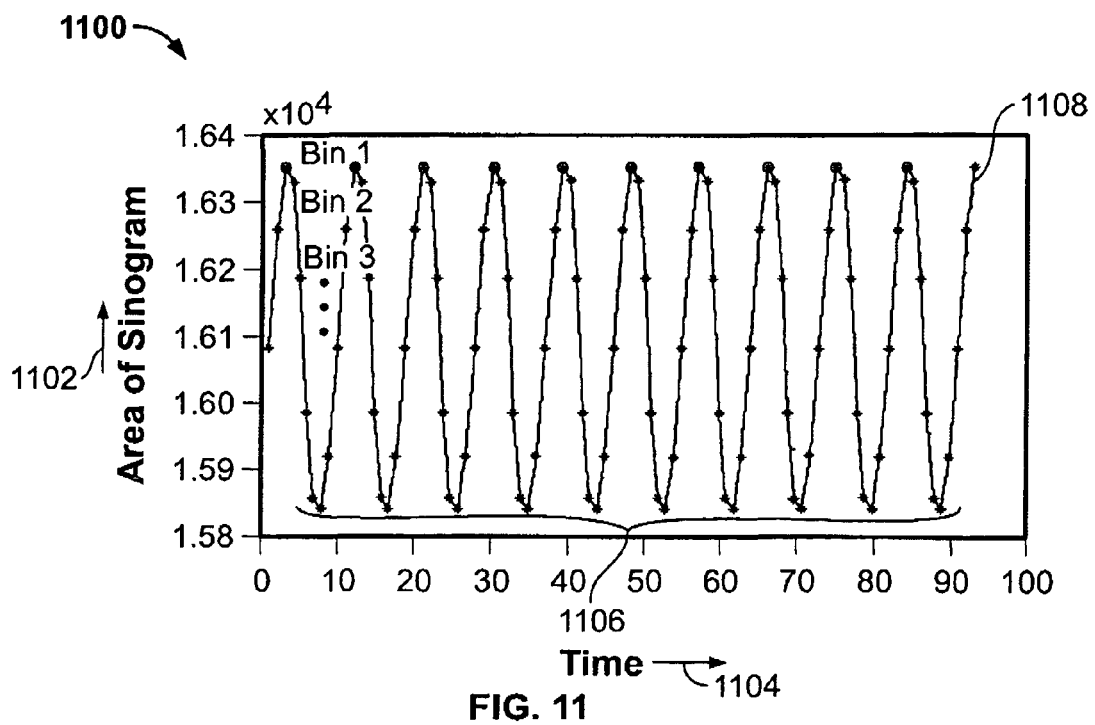
FIG. 11 is a phantom fixed forward binning graph formed in accordance with an embodiment of the present invention.

FIG. 11 is a phantom fixed forward binning graph 1100 formed in accordance with an embodiment of the present invention. An area 1102 of multiple sinograms over a time 1104 is plotted to produce ten respiratory cycles 1106. The peaks of the waveform 1108, representing the start of expiration, are detected; and these data points are placed in bin 1. Depending on the number of bins specified, data points are placed in successive bins until another peak is detected.

Figure 12:
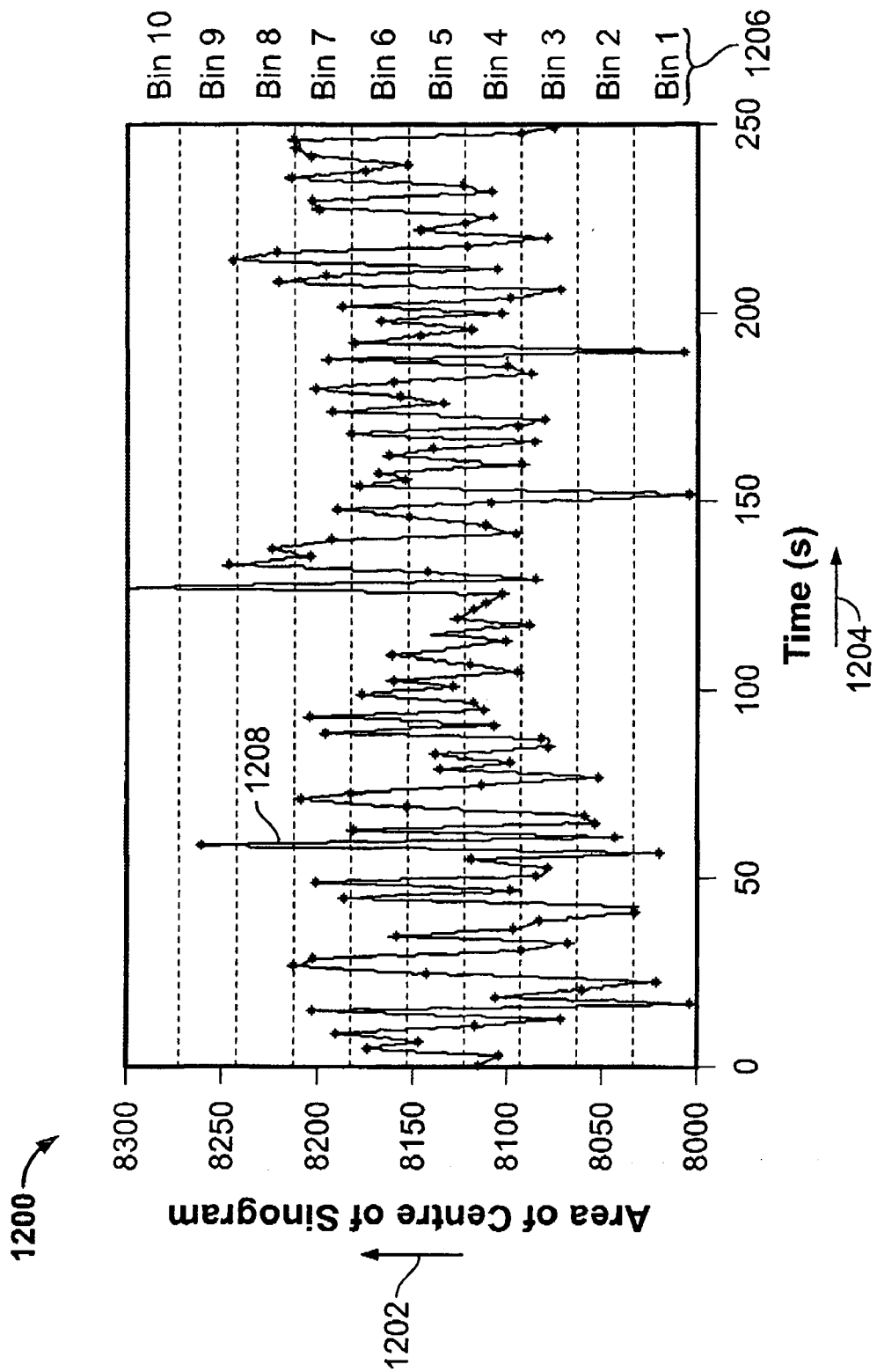
FIG. 12 is an amplitude data set graph formed in accordance with an embodiment of the present invention.

FIG. 12 is an amplitude data set graph 1200 formed in accordance with an embodiment of the present invention. Using patient data, a center area 1202 of multiple sinograms over a time 1204 is plotted to generate a waveform 1208 of varying amplitude. The sinogram data can be binned at 1206 into the respective respiratory cycles using at least one of amplitude and phase.

The analysis described above may be performed on several different data sets. Calculations may be performed on individual slices or rings of detectors, groups of slices, all slices, or a select line of responses, specific r and Ø ranges, etc. The analyzed data set may be modified to focus on the motion of specific organs or structures. The physiological structure may include a biological organ, for example, the stomach, heart, lung or liver; a biological structure, for example, the diaphragm, chest wall, rib cage, rib, spine, sternum or pelvis; or a foreign object fiducial marker, for example, a marker placed for the purpose of gating according to the prescribed method of the invention; a tumor; or a lesion or sore, for example, a bone compression fracture.

While the invention has been described in terms of various specific embodiments, those skilled in the art will recognize that the invention can be practiced with modification within the spirit and scope of the claims.

What is claimed is:

1. A method of imaging an object using a medical imaging system, said method comprising:
   acquiring a stream of sinogram data;
   detecting changes in the stream of sinogram data corresponding to movement of the object, wherein said detecting changes in the stream of sinogram data further comprises binning the stream of sinogram data into at least one sinogram, detecting edges of the sinogram data in the sinogram and based thereon computing at least one area related parameter of the sinogram data;
   selecting at least one portion of the stream of sinogram data based on the area-related parameter; and
   generating and displaying an image of the object based on the selected portions of the stream of sinogram data.

2. The method of claim 1 wherein said acquiring includes performing a positron emission tomography (PET) scan of the object.

3. The method of claim 1 wherein said acquiring includes performing a computed tomography (CT) scan of the object.

4. The method of claim 1 wherein said detecting changes in the stream of sinogram data further comprises filtering the sinogram data in multiple dimensions, including time, space and volume of the sinogram data, prior to detection of changes.

5. The method of claim 1 wherein said detecting changes in the stream of sinogram data further comprises computing at least one of a minimum width, maximum width, and average width of the sinogram data.

6. The method of claim 1 wherein said detecting changes in the stream of sinogram data further comprises calculating an area of at least a portion of the acquired data in the sinogram.

7. The method of claim 1 wherein said detecting changes in the stream of sinogram data further comprises binning the stream of sinogram data into a sinogram at a discrete time interval and determining at least one of a center area, a z-centroid, and a y-centroid, of the acquired data in the sinogram.

8. The method of claim 1 wherein said detecting changes in the stream of sinogram data further comprises binning the stream of sinogram data into a sinogram at a discrete time interval and computing at least one of a linear regression coefficient r-squared of the edges of the acquired data in the sinogram and a sum of the square of the difference of the edges of the acquired data in the sinogram.

9. The method of claim 1 wherein said detecting changes in the stream of sinogram data further comprises initial accumulation of entire duration of sinogram data (over a plurality of respiratory cycles) and computing an average sinogram envelope and then binning the stream of sinogram data into a sinogram at a specific slice or slab location and at a discrete time interval and computing a local sinogram envelope and computing the deviation above or below the average sinogram envelope.

10. The method of claim 1 further comprising detecting changes in the images reconstructed from the binned image data.

11. The method of claim 1 wherein said detecting changes in the stream of sinogram data further comprises binning the stream of sinogram data into a sinogram and reconstructing a PET image.

12. The method of claim 1 further comprising binning the stream of sinogram data into a sinogram; reconstructing the PET image; and detecting changes in the reconstructed PET image.

13. The method of claim 1 wherein said detecting changes in the stream of image data further comprises binning the stream of sinogram data into a sinogram; reconstructing the PET image; and detecting changes in the reconstructed PET image data further comprising filtering the reconstructed image data in multiple dimensions, including time, space and volume of the sinogram data, prior to detection of changes.

14. The method of claim 1 wherein said detecting changes in the stream of sinogram data further comprises detecting changes in at least one reconstructed CT image at discrete time intervals corresponding to the stream of sinogram data.

15. The method of claim 1 wherein said generating an image further comprises dividing a respiratory cycle into respiratory time intervals based on said detected changes in the stream of sinogram data and rebinning the at least one sinogram into a corresponding said respiratory time interval associated with physiological movement of the object based on said detected changes.

16. A medical imaging system, comprising:
a scanner configured to acquire a stream of sinogram data;
a processor configured to bin the stream of sinogram data into at least two sinograms, detect changes between the at least two sinograms corresponding to movement of an object by computing at least one area related parameter of the sinogram data, and select portions of the stream of sinogram data based on the area-related parameter; and
an image processor configured to generate an image of the object based on the selected portions of the stream of sinogram data, said image processor rebinning the stream of sinogram data according to at least one of the detected changes, a bin corresponding to a time interval associated with physiological movement of the object.

17. The system of claim 16 wherein said scanner is a positron emission tomography (PET) scanner.

18. The system of claim 16 wherein said scanner is a computed tomography (CT) scanner.

19. The system of claim 16 wherein said scanner is a Nuclear Computed Tomography (SPECT) scanner.

20. The system of claim 16 wherein the detecting of changes in the stream of sinogram data include binning of the stream of sinogram data into a sinogram and at least one of measuring a minimum width, calculating an area, calculating a center area, determining a y-centroid, determining a z-centroid of the sinogram data, computing the deviation of the sinogram envelope from an average sinogram over multiple respiratory cycles, computing a linear regression r squared of the edges, and calculating a sum of the difference of the edges of the acquired data in the sinogram.

21. The system of claim 16 wherein the detecting of changes in the stream of sinogram data includes measuring changes in simultaneous second modality reconstructed images including CT, x-ray and ultrasound.

22. A method for generating an image of an object using at least one of a positron emission tomography (PET) system or a positron emission tomography/computed tomography (PET/CT) system, said method comprising:
scanning an object to acquire a stream of sinogram data using the PET system or the PET/CT system;
storing the stream of sinogram data;
detecting changes in the stored stream of sinogram data corresponding to movement of the object in a respiratory cycle, wherein said detecting changes in the stream of sinogram data further comprises binning the stream of sinogram data into at least one sinogram and computing at least one area related parameter of the sinogram data;
selecting at least one portion of the stored stream of sinogram data based on the area-related parameter; and
generating and displaying an image of the object based on the selected portions of the stored stream of sinogram data, wherein the respiratory cycle is divided into time intervals based on said detected changes, and portions of the stored stream of sinogram data associated with the time intervals of the respiratory cycle are gated into associated bins.

23. The method of claim 22 wherein said detecting changes in the stream of sinogram data further comprises detecting changes in at least one of a stored reconstructed PET image data set and a stored reconstructed PET/CT image data set.

24. The method of claim 22 wherein said scanning includes acquiring lines of response data for generating separate sinograms.

25. The method of claim 22 wherein said storing includes generating from the acquired stream of sinogram data separate sinograms for direct planes and cross planes in 2-dimension (2D), and separate sinograms for all possible planes in 3-dimension (3D).

26. The method of claim 22 wherein the respiratory cycle is divided into time intervals based on said detected changes, and portions of the stored stream of sinogram data associated with the time intervals of the respiratory cycle are gated into associated bins.

27. The method of claim 22 further comprising determining time intervals from a predetermined number of sinograms, each sinogram classified by at least one of minimum width, area, center area, z-centroid shift, y-centroid shift, linear regression r squared of the edges, deviation of sinogram envelope from an average sinogram envelope over multiple respiratory cycles, and sum of square of difference of the edges, into a specific respiratory phase.

28. The method of claim 22 wherein said generating includes binning the stored stream of sinogram data into respective phases of the respiratory cycle using at least one of amplitude and phase.

29. The method of claim 22 wherein said generating includes binning the stored stream of sinogram data into respective phases of the respiratory cycle using a fixed forward method of binning involving a trigger at the start of the signal and sequential binning according to time from trigger.

30. The method of claim 22 wherein said generating includes binning the stored stream of sinogram data into respective phases of the respiratory cycle using a percentage method of binning involving a trigger at the start of the signal and sequential binning according to a proportion of data from trigger.

31. The method of claim 22 further comprising displaying gated sinograms over successive time intervals to produce a simulation of physiological movement.

32. The method of claim 22 further comprising displaying gated sinograms over successive time intervals to produce a representation of physiological motion, said representation used for diagnosis of respiratory events.

33. The method of claim 22 further comprising displaying gated phantom images of a physiological structure after image reconstruction over successive time intervals to produce a simulation of physiological movement.

34. The method of claim 22 further comprising displaying gated phantom images of a physiological structure after image reconstruction over successive time intervals to produce a representation of physiological motion, said representation used for diagnosis of respiratory events.

35. The method of claim 33 wherein the physiological structure includes at least one of a biological organ, a biological structure, a foreign object fiducial marker, a tumor, and a lesion.

36. The method of claim 22 wherein said storing includes storing the acquired stream of sinogram data in a list mode, the list mode representing capture of detected coincidence events in a form of a chronologically ordered event list for playback with a different frame or bin size.

* * * * *

UNITED STATES PATENT AND TRADEMARK OFFICE
CERTIFICATE OF CORRECTION

PATENT NO. : 7,574,249 B2  Page 1 of 1
APPLICATION NO. : 11/053793
DATED : August 11, 2009
INVENTOR(S) : Piacsek et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 526 days.

Signed and Sealed this

Seventh Day of September, 2010

David J. Kappos
*Director of the United States Patent and Trademark Office*